(12) United States Patent
Barbosa et al.

(10) Patent No.: US 11,850,131 B2
(45) Date of Patent: Dec. 26, 2023

(54) PERSONAL HYGIENE PRODUCT WITH A DIGITAL ELEMENT

(71) Applicant: Johnson & Johnson Consumer Inc., Skillman, NJ (US)

(72) Inventors: Livea Barbosa, São José dos Campos (BR); Jose Francisco Cau, São José dos Campos (BR); Rafael Carniato, Caçapava (BR); Mariana Goulart, Herrsching am Ammersee (DE); William Chester Neeley, Melbourne, FL (US); Renato Pereira, São José dos Campos (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 368 days.

(21) Appl. No.: 16/954,623

(22) PCT Filed: Dec. 21, 2018

(86) PCT No.: PCT/US2018/067004
§ 371 (c)(1),
(2) Date: Jun. 17, 2020

(87) PCT Pub. No.: WO2019/126606
PCT Pub. Date: Jun. 27, 2019

(65) Prior Publication Data
US 2020/0306102 A1 Oct. 1, 2020

Related U.S. Application Data

(60) Provisional application No. 62/608,836, filed on Dec. 21, 2017.

(51) Int. Cl.
*A61F 13/42* (2006.01)
*A61F 13/472* (2006.01)
(Continued)

(52) U.S. Cl.
CPC ............ *A61F 13/42* (2013.01); *A61F 13/472* (2013.01); *A61F 13/511* (2013.01); *A61F 13/84* (2013.01);
(Continued)

(58) Field of Classification Search
CPC ...... A61F 13/42; A61F 13/472; A61F 13/511; A61F 13/84; A61F 2013/424; A61F 2013/429; A61F 2013/8479
See application file for complete search history.

(56) References Cited

U.S. PATENT DOCUMENTS 3,911,173 A * 10/1975 Sprague, Jr. ......... A43D 25/183
427/256
4,163,449 A * 8/1979 Regal ........................ A61F 5/48
340/573.5
(Continued)

FOREIGN PATENT DOCUMENTS

| EP | 2654646 B | 7/2016 |
| EP | 3061433 A | 8/2016 |

(Continued)

OTHER PUBLICATIONS

Rahman et al., A Low-Cost wet Diaper Detector Based on Smart Phone and BLE Sensor (Year: 2017).*
(Continued)

*Primary Examiner* — Quang Pham

(57) ABSTRACT

A personal hygiene product with a digital element includes an external personal hygiene product to absorb bodily fluids and a conductive sensor assembly disposed therein. The conductive sensor assembly includes a pair of conductive elements disposed in parallel in a mirrored image about the perimeter of the personal hygiene product and at least one connector directly contacting the pair of conductive elements, said conductive sensor assembly generating a signal indicative of fluid leakage of said personal hygiene product (Continued)

when fluid reaches the area between the pair of conductive elements. The conductive sensor assembly is arranged and configured to communicate with a smart hand held electronic device, either directly or through a wireless connection.

12 Claims, 8 Drawing Sheets

(51) Int. Cl.
*A61F 13/511* (2006.01)
*A61F 13/84* (2006.01)

(52) U.S. Cl.
CPC ... *A61F 2013/424* (2013.01); *A61F 2013/429* (2013.01); *A61F 2013/8479* (2013.01)

(56) References Cited

U.S. PATENT DOCUMENTS

| | | | | |
|---|---|---|---|---|
| 4,800,370 A * | 1/1989 | Vetecnik | A61F 13/42 340/573.5 |
| 4,977,906 A * | 12/1990 | Di Scipio | A61F 13/42 128/885 |
| 5,291,181 A * | 3/1994 | DePonte | A61F 13/42 340/573.6 |
| 5,459,452 A * | 10/1995 | DePonte | A61F 13/42 340/573.5 |
| 5,760,694 A * | 6/1998 | Nissim | A61F 13/42 128/885 |
| 5,790,036 A * | 8/1998 | Fisher | A61F 13/42 340/573.5 |
| 5,796,345 A * | 8/1998 | Leventis | A61F 13/42 429/118 |
| 5,844,862 A * | 12/1998 | Cocatre-Zilgien | A61B 5/411 600/509 |
| 5,868,723 A * | 2/1999 | Al-Sabah | A61F 13/42 340/573.5 |
| 5,904,671 A * | 5/1999 | Navot | A61F 13/42 340/573.5 |
| 6,014,346 A * | 1/2000 | Malone | G04F 1/005 600/595 |
| 6,075,178 A * | 6/2000 | La Wilhelm | A61F 13/42 604/361 |
| 6,163,262 A * | 12/2000 | Wu | A61F 13/42 340/384.1 |
| 6,186,991 B1 * | 2/2001 | Roe | A61L 15/20 604/385.12 |
| 6,246,330 B1 * | 6/2001 | Nielsen | A61F 13/42 340/384.1 |
| 6,407,308 B1 * | 6/2002 | Roe | A61L 15/18 604/362 |
| 6,603,403 B2 * | 8/2003 | Jeutter | A61F 13/42 340/941 |
| 6,870,479 B2 * | 3/2005 | Gabriel | G16H 40/67 200/182 |
| 6,917,293 B2 * | 7/2005 | Beggs | G08B 21/22 340/666 |
| 7,250,547 B1 * | 7/2007 | Hofmeister | G01N 27/121 340/573.5 |
| 7,355,090 B2 * | 4/2008 | Ales, III | A61F 13/42 340/573.5 |
| 7,394,391 B2 * | 7/2008 | Long | A61F 13/42 340/573.5 |
| 7,449,614 B2 * | 11/2008 | Ales, III | A61F 13/8405 604/362 |
| 7,477,156 B2 * | 1/2009 | Long | A61F 13/42 340/573.5 |
| 7,498,478 B2 * | 3/2009 | Long | A61F 13/42 604/385.01 |
| 7,522,061 B2 * | 4/2009 | Rondoni | A61B 5/14507 604/362 |
| 7,603,131 B2 * | 10/2009 | Wang | H04W 4/02 707/999.005 |
| 7,642,396 B2 * | 1/2010 | Ales, III | A61F 13/84 340/573.5 |
| 7,649,125 B2 * | 1/2010 | Ales, III | A61F 13/42 340/573.5 |
| 7,806,882 B1 * | 10/2010 | Larkin | A61F 13/2051 604/385.18 |
| 7,812,731 B2 * | 10/2010 | Bunza | A61F 13/42 340/573.5 |
| 7,834,235 B2 * | 11/2010 | Long | A61F 13/42 340/573.5 |
| 7,855,653 B2 * | 12/2010 | Rondoni | A61B 5/6808 340/573.5 |
| 7,977,529 B2 * | 7/2011 | Bergman | G16H 40/60 703/11 |
| 8,044,258 B2 | 10/2011 | Hietpas et al. | |
| 8,057,454 B2 * | 11/2011 | Long | A61F 13/42 604/361 |
| 8,264,362 B2 * | 9/2012 | Ales, III | A61F 13/42 340/572.1 |
| 8,412,297 B2 * | 4/2013 | Mannheimer | A61B 5/6814 600/340 |
| 8,421,636 B2 * | 4/2013 | Collette | A61F 13/42 340/573.5 |
| 8,515,515 B2 * | 8/2013 | McKenna | A61B 5/14552 600/323 |
| 8,558,053 B2 * | 10/2013 | Roe | A61F 13/49019 604/385.03 |
| 8,604,268 B2 * | 12/2013 | Cohen | A61F 13/42 604/361 |
| 8,628,506 B2 * | 1/2014 | Ales, III | A61F 13/84 604/361 |
| 8,697,933 B2 * | 4/2014 | Ales, III | G16H 40/63 604/361 |
| 9,314,381 B2 | 4/2016 | Curran et al. | |
| 9,333,118 B2 | 5/2016 | Elfström et al. | |
| 9,408,757 B2 * | 8/2016 | Elfström | A61F 13/42 |
| 9,545,342 B2 * | 1/2017 | Cretu-Petra | A61B 5/6802 |
| 9,655,787 B2 * | 5/2017 | Wilson | A61F 13/42 |
| 9,901,488 B1 * | 2/2018 | Levin | A61B 5/1116 |
| 10,117,790 B2 | 11/2018 | Pugh et al. | |
| 10,130,524 B1 * | 11/2018 | Lai | G08B 13/19669 |
| 10,271,998 B2 * | 4/2019 | LaVon | A61F 13/58 |
| 10,285,871 B2 * | 5/2019 | Arizti | A61F 13/64 |
| 10,492,959 B2 * | 12/2019 | Yi | A61F 13/42 |
| 10,603,224 B2 * | 3/2020 | Prokopuk | A61F 13/42 |
| 10,624,795 B2 * | 4/2020 | Christiansen | A61F 13/42 |
| 10,674,940 B2 * | 6/2020 | Kilcran | G08B 5/36 |
| 10,687,988 B2 * | 6/2020 | Morimoto | A61F 13/84 |
| 10,828,207 B2 * | 11/2020 | Long | A61F 13/49 |
| 10,905,371 B2 * | 2/2021 | Brief | A61B 5/4318 |
| 11,013,641 B2 * | 5/2021 | Sullivan | A61F 13/84 |
| 11,022,511 B2 * | 6/2021 | Kain | G01L 9/0051 |
| 11,051,996 B2 * | 7/2021 | Arizti | A61B 5/0024 |
| 11,229,557 B2 * | 1/2022 | Kurt | A61F 13/513 |
| 11,617,689 B2 * | 4/2023 | Kurt | A61F 13/53 340/539.11 |
| 2001/0044588 A1 * | 11/2001 | Mault | A61B 5/073 374/E1.004 |
| 2002/0003478 A1 * | 1/2002 | Zhao | G08B 21/20 340/604 |
| 2003/0155241 A1 * | 8/2003 | Lai | G01N 27/4045 204/461 |
| 2004/0064114 A1 | 4/2004 | David et al. | |
| 2004/0147888 A1 * | 7/2004 | Huang | A61F 13/42 604/361 |
| 2004/0207530 A1 * | 10/2004 | Nielsen | A61F 13/42 340/573.5 |
| 2005/0096612 A1 * | 5/2005 | Davis | A61F 13/42 604/361 |
| 2005/0156744 A1 * | 7/2005 | Pires | A61F 13/42 340/573.5 |
| 2005/0270162 A1 * | 12/2005 | Hsieh | A61F 13/42 340/573.5 |
| 2006/0061477 A1 * | 3/2006 | Yeh | A61F 13/42 340/573.5 |

(56) References Cited

U.S. PATENT DOCUMENTS

| | | | |
|---|---|---|---|
| 2006/0229577 A1* | 10/2006 | Roe | A61F 13/42 604/361 |
| 2006/0247590 A1* | 11/2006 | Ito | A61F 13/474 604/378 |
| 2006/0264858 A1* | 11/2006 | Roe | A61F 13/42 604/361 |
| 2006/0290517 A1* | 12/2006 | Cohen | A61F 13/84 340/573.1 |
| 2007/0204691 A1* | 9/2007 | Bogner | A61B 5/6892 73/432.1 |
| 2007/0252712 A1* | 11/2007 | Allen | A61F 13/42 340/573.5 |
| 2007/0252713 A1* | 11/2007 | Rondoni | A61B 5/6808 340/573.5 |
| 2007/0260209 A1* | 11/2007 | Brilman | A61B 5/6804 116/109 |
| 2007/0287971 A1* | 12/2007 | Roe | A61F 13/42 604/361 |
| 2008/0036614 A1* | 2/2008 | Gabriel | A61F 13/42 340/604 |
| 2008/0071239 A1* | 3/2008 | Nandrea | A61F 13/42 604/378 |
| 2008/0150730 A1* | 6/2008 | Hsu | A61B 5/0878 340/584 |
| 2008/0195072 A1* | 8/2008 | Warner | A61L 15/56 604/385.01 |
| 2008/0234644 A1* | 9/2008 | Hansson | A61L 15/56 604/360 |
| 2008/0266117 A1* | 10/2008 | Song | A61F 13/42 340/573.5 |
| 2008/0266123 A1* | 10/2008 | Ales | A61F 13/42 343/720 |
| 2008/0278337 A1* | 11/2008 | Huang | A61F 13/42 340/573.5 |
| 2009/0036856 A1* | 2/2009 | Woltman | A61F 13/15 604/385.04 |
| 2009/0062758 A1* | 3/2009 | Ales, III | A61F 13/42 604/362 |
| 2009/0315720 A1* | 12/2009 | Clement | H01Q 1/2225 340/573.5 |
| 2009/0321238 A1* | 12/2009 | Nhan | H01B 1/24 200/534 |
| 2009/0326492 A1* | 12/2009 | Hietpas | A61F 13/42 604/361 |
| 2010/0160882 A1 | 6/2010 | Lowe | |
| 2010/0164733 A1* | 7/2010 | Ales | A61F 13/42 340/604 |
| 2010/0168694 A1* | 7/2010 | Gakhar | G01N 21/3554 604/361 |
| 2010/0168702 A1* | 7/2010 | Ales, III | A61F 13/42 604/361 |
| 2010/0241094 A1* | 9/2010 | Sherron | A61F 13/42 604/361 |
| 2010/0305530 A1* | 12/2010 | Larkin | A61F 13/2051 604/361 |
| 2010/0324520 A1* | 12/2010 | Roe | A61F 13/51496 604/385.16 |
| 2010/0328075 A1* | 12/2010 | Rahamim | A61B 5/1135 340/573.1 |
| 2010/0331630 A1* | 12/2010 | Odio | A61B 5/1118 600/301 |
| 2012/0092027 A1* | 4/2012 | Forster | G05D 22/02 29/829 |
| 2012/0150072 A1* | 6/2012 | Revol-Cavalier | A61B 5/4266 600/573 |
| 2012/0206265 A1* | 8/2012 | Solazzo | A61F 13/42 340/573.5 |
| 2012/0256750 A1* | 10/2012 | Novak | A61F 13/42 340/573.5 |
| 2012/0310192 A1* | 12/2012 | Suzuki | A61F 13/42 604/361 |
| 2012/0323194 A1* | 12/2012 | Suzuki | A61F 13/42 204/403.01 |
| 2013/0012896 A1* | 1/2013 | Suzuki | G16H 40/63 604/361 |
| 2013/0041334 A1* | 2/2013 | Prioleau | A61F 13/42 604/361 |
| 2013/0076509 A1* | 3/2013 | Ahn | A61F 13/42 340/539.12 |
| 2013/0110061 A1* | 5/2013 | Abraham | A61F 13/42 604/342 |
| 2013/0110063 A1* | 5/2013 | Abraham | G16H 40/67 604/361 |
| 2013/0110064 A1* | 5/2013 | Richardson | A61F 13/42 340/573.5 |
| 2013/0123726 A1* | 5/2013 | Yu | H01Q 1/273 235/492 |
| 2013/0131618 A1* | 5/2013 | Abraham | A61F 13/42 604/361 |
| 2013/0144237 A1* | 6/2013 | Abraham | A61F 13/42 604/361 |
| 2013/0233063 A1* | 9/2013 | Wang | A61F 13/42 73/73 |
| 2013/0254141 A1* | 9/2013 | Barda | A61F 13/42 706/46 |
| 2013/0292264 A1* | 11/2013 | Hou | G01N 27/223 73/1.06 |
| 2013/0303867 A1* | 11/2013 | Elfstrom | A61F 13/42 604/361 |
| 2013/0331666 A1* | 12/2013 | Miller | G01N 33/528 29/428 |
| 2014/0069170 A1* | 3/2014 | Seo | G01N 27/121 73/29.05 |
| 2014/0071818 A1* | 3/2014 | Wang | H04W 4/029 370/230 |
| 2014/0121487 A1* | 5/2014 | Faybishenko | G16H 40/63 600/365 |
| 2014/0135722 A1* | 5/2014 | Dougherty, Jr. | A61F 13/42 604/361 |
| 2014/0148772 A1* | 5/2014 | Hu | A61F 13/42 604/385.01 |
| 2014/0155850 A1* | 6/2014 | Shah | A61F 13/42 604/361 |
| 2014/0188063 A1* | 7/2014 | Nhan | A61F 13/00055 604/361 |
| 2014/0259483 A1* | 9/2014 | Cheng | B32B 5/08 15/104.93 |
| 2014/0276503 A1* | 9/2014 | Sheldon | A61F 13/535 604/389 |
| 2014/0323912 A1* | 10/2014 | Minoguchi | A61F 13/42 600/574 |
| 2014/0333441 A1* | 11/2014 | Solazzo | A61F 13/42 340/573.5 |
| 2014/0371702 A1* | 12/2014 | Bosaeus | A61F 13/51484 604/385.01 |
| 2014/0375297 A1* | 12/2014 | Geiger | A61F 13/42 604/361 |
| 2015/0080819 A1* | 3/2015 | Charna | A61F 13/42 604/361 |
| 2015/0150732 A1* | 6/2015 | Abir | A61F 13/42 356/445 |
| 2015/0157512 A1* | 6/2015 | Abir | A61B 5/08 340/573.5 |
| 2015/0164703 A1* | 6/2015 | Bae | A61F 13/42 324/693 |
| 2015/0223755 A1* | 8/2015 | Abir | A61B 90/30 600/300 |
| 2015/0257942 A1* | 9/2015 | Kim | G08B 25/10 604/361 |
| 2015/0320609 A1* | 11/2015 | Thoen | A61F 13/42 340/573.5 |
| 2015/0352357 A1* | 12/2015 | Wei | A61N 1/0456 604/385.03 |
| 2015/0359689 A1* | 12/2015 | Carney | A61B 5/6804 600/367 |
| 2016/0095758 A1* | 4/2016 | Haire | A61B 5/002 600/595 |

(56) References Cited

U.S. PATENT DOCUMENTS

| | | | |
|---|---|---|---|
| 2016/0120455 A1* | 5/2016 | Pop | A61F 13/42 600/301 |
| 2016/0166438 A1* | 6/2016 | Rovaniemi | A61F 13/42 493/320 |
| 2016/0250081 A1* | 9/2016 | Pugh | G08B 21/182 604/361 |
| 2016/0374867 A1* | 12/2016 | Zand | A61F 13/42 604/361 |
| 2016/0374868 A1 | 12/2016 | Ettrup | |
| 2017/0035622 A1* | 2/2017 | Wang | A61F 13/42 |
| 2017/0071803 A1* | 3/2017 | Wu | A61B 5/0205 |
| 2017/0098872 A1* | 4/2017 | Sood | H01M 10/482 |
| 2017/0112681 A1* | 4/2017 | Mancini | A61F 13/42 |
| 2017/0128275 A1* | 5/2017 | Tanio | A61F 13/539 |
| 2017/0135877 A1* | 5/2017 | Kudo | A61F 13/4756 |
| 2017/0165123 A1* | 6/2017 | Gogin | A61L 15/56 |
| 2017/0165125 A1* | 6/2017 | Turner | A61F 13/496 |
| 2017/0199143 A1* | 7/2017 | Nebuya | A61M 1/14 |
| 2017/0236398 A1 | 8/2017 | Eddy et al. | |
| 2017/0249602 A1* | 8/2017 | Robertson | G06Q 10/30 |
| 2017/0340254 A1* | 11/2017 | Davis | A61B 5/15087 |
| 2018/0008478 A1* | 1/2018 | Xu | A61F 13/42 |
| 2018/0011080 A1* | 1/2018 | Xu | A61B 5/0008 |
| 2018/0021183 A1* | 1/2018 | Teng | A61F 13/49 604/361 |
| 2018/0036180 A1* | 2/2018 | Long | A61F 13/49004 |
| 2018/0055697 A1* | 3/2018 | Mihali | A61F 13/42 |
| 2018/0085262 A1* | 3/2018 | Schwirian | G06K 19/0723 |
| 2018/0104114 A1* | 4/2018 | Pepin | G01N 27/048 |
| 2018/0104115 A1* | 4/2018 | Collette | A61F 13/42 |
| 2018/0149635 A1* | 5/2018 | Abir | A61F 13/42 |
| 2018/0177644 A1* | 6/2018 | Tuli | A61F 13/42 |
| 2018/0325743 A1* | 11/2018 | Ho | A61F 13/42 |
| 2018/0368814 A1* | 12/2018 | R. Kudtarkar | A61B 5/4318 |
| 2019/0105210 A1* | 4/2019 | Pugh | A61B 5/24 |
| 2019/0110938 A1* | 4/2019 | Chiu | G01N 27/121 |
| 2019/0133524 A1* | 5/2019 | Dong | A61B 5/6808 |
| 2019/0154607 A1* | 5/2019 | Tuli | G01N 27/07 |
| 2019/0167490 A1* | 6/2019 | Hellmold | A61F 13/15699 |
| 2019/0287678 A1* | 9/2019 | Stevens | A61B 5/746 |
| 2020/0046573 A1* | 2/2020 | Douseki | G01N 27/416 |
| 2020/0060899 A1 | 2/2020 | Neeley et al. | |
| 2020/0256819 A1* | 8/2020 | Curran | A61F 13/42 |
| 2020/0276063 A1* | 9/2020 | Muñoz Herencia | A61F 13/58 |
| 2020/0337880 A1* | 10/2020 | Hansen | A61F 5/443 |
| 2022/0233363 A1* | 7/2022 | Heirman | A61F 13/49 |

FOREIGN PATENT DOCUMENTS

| | | |
|---|---|---|
| WO | WO 2010/076679 A | 7/2010 |
| WO | WO 2010/123425 A | 10/2010 |
| WO | WO 2012/084985 A | 6/2012 |
| WO | WO 2013/097899 A | 7/2013 |

OTHER PUBLICATIONS

Siden et al., The smart diaper moisture detection system (Year: 2004).*

Ngo et al., A Novel Low Cost Wireless Incontinence Sensor System (Screen-Printed Flexible Sensor System) for Wireless Urine Detection in Incontinence Materials (Year: 2018).*

Uddin et al., Smart Diaper Non-stop Diaper Monitoring System (Year: 2021).*

Lin et al., Design and Fabrication of Smart Diapers with Antibacterial Yarn (Year: 2017).*

Banchajarurat et al., Development of Smart Diaper with 3D Printed Sensor-Supporter for Elderly Care (Year: 2019).*

U.S. Appl. No. 15/045,663, filed Feb. 17, 2016, US2016-0250081A1, Sep. 1, 2016, U.S. Pat. No. 10,117,790, Nov. 6, 2018, Grant.

U.S. Appl. No. 62/121,463, filed Feb. 26, 2015, Expired.

U.S. Appl. No. 16/106,463, filed Aug. 21, 2018, US2020-0060899A1, Feb. 27, 2020, Pending.

U.S. Appl. No. 16/130,403, filed Sep. 13, 2018, US2019-0150210A1, Apr. 11, 2019, Pending.

U.S. Appl. No. 62/569,744, filed Oct. 9, 2017, Expired.

International search report and written opinion dated Mar. 27, 2019, for international application PCT/US2018/067004.

\* cited by examiner

PERSONAL HYGIENE PRODUCT WITH A DIGITAL ELEMENT

CROSS-REFERENCE TO RELATED APPLICATIONS

This application is the national stage filing under 35 USC 371 of international application PCT/US2018/067004 filed on Dec. 21, 2018, which claims the benefit of U.S. provisional application 62/608,836 filed on Dec. 21, 2017, the complete disclosure of which is hereby incorporated herein by reference for all purposes.

BACKGROUND OF THE INVENTION

1. Field of the Invention

This relates to personal hygiene products used for personal care, primarily for absorption or containment of bodily fluid, and more particularly, to an external personal hygiene product with a digital element that may be utilized to sense and wirelessly communicate discharge related data to the user via a smart hand held electronic device.

2. Discussion of the Related Art

The basic structure of a personal hygiene product has not varied greatly over time. The needs of users have also not varied: to prevent seepage onto the skin, clothing, or external environment through maximized absorption and predictability of the personal hygiene product's absorption capacity. External personal hygiene products include bed pads, disposable adult diapers, disposable adult briefs, disposable sanitary napkins, sanitary napkins with adhesive strips and wings, panty liners, and nursing pads. Most people will at some point in their life use a personal hygiene product for a period of time. Personal hygiene products historically involve a one-size-fits-all approach.

A woman, for example will use an estimated average of 10,000 personal hygiene products in a lifetime. Even though feminine hygiene products come in different sizes and shapes designed for varying absorbent capacity, no product is 100 percent effective in preventing spills or leakage because variance in menstruation may lead to oversaturation. Each woman's menstrual flow varies over the course of her menstruation, with some days being lighter or heavier than others. Because of menstrual variance, accidents or overflows may occur where the personal hygiene product becomes oversaturated and spills outside of the absorbent area. Continued use of an oversaturated hygiene product may lead to negative health impacts such as bacterial infections or toxic shock syndrome.

Many women manually track or monitor their menstrual cycle for predictability to avoid the unexpected start of menstruation in the absence of a personal hygiene product or accidents of the sort discussed above. There are over two hundred smart device applications available to monitor menstruation manually. Users enter data into the application on a smart device, for example a smart phone or other hand-held device, and the application generates data predicting, for example, menstrual start day, flow pattern, and length of menstruation. Many of these smart device applications issue alerts when menstruation is expected to start and end. All available devices, however, rely on data based on the subjective and manual entry of the user and may not reliably meet the primary needs most female hygiene product users have: predictability and reliability. None of these applications are able to actively monitor the active absorption capacity of a personal hygiene product while a user is wearing or using it.

In addition to the need for predictability and reliability in use of a personal hygiene product, a personal hygiene product is situated either proximate to or inserted into the body and as a result is able to collect data about patterns of discharge and biometrics in a way that a manual-entry application is unable to capture. This data is beneficial, to avoid social embarrassment, and also for a user's overall health, for example, to provide accurate data to a physician or to alert the user if there are disruptions in normal patterns of bodily fluid discharge.

The proper combination of a personal hygiene product incorporated with a digital element capable of interfacing with a smart hand held electronic device would meet the ultimate needs of personal hygiene product consumers. The digital element needs to biocompatible and comprised of an array capable of wireless communication. Accordingly, there exists a need for providing a personal hygiene product capable of gathering, processing, and communicating data about the product's absorbent capacity and individual user's bodily fluid discharge to smart hand held electronic device of a user. There are also exists a need for an individual user to be able to interface with the data once communicated to the smart hand held electronic device.

External personal hygiene products have been proposed with a parallel conductive track about an absorbent structure, such as in U.S. Pat. Nos. 8,044,258 and 9,408,757. However, the signal from a parallel conductive track provides a variable signal, depending upon where the circuit between the parallel tracks bridges. Thus, it can be difficult to determine noise from actual potential leakage.

Accordingly, the need exists for novel conductive track for external personal hygiene products that provides a clear signal when failure of the product is imminent.

SUMMARY OF THE INVENTION

A personal hygiene product with a digital element in accordance with the present invention overcomes the limitations with the prior art as briefly discussed above.

We have determined that a personal hygiene product with a digital element is an improvement of the existing state of the art. In particular, personal hygiene product with a digital element includes an external personal hygiene product to absorb bodily fluids and a conductive sensor assembly disposed therein. The conductive sensor assembly includes a pair of conductive elements disposed in parallel in a mirrored image about the perimeter of the personal hygiene product and at least one connector directly contacting the pair of conductive elements, said conductive sensor assembly generating a signal indicative of fluid leakage of said personal hygiene product when fluid reaches the area between the pair of conductive elements. The conductive sensor assembly is arranged and configured to communicate with a smart hand held electronic device, either directly or through a wireless connection.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

A device comprising a hygiene product with a digital element capable of interface with a smart hand held electronic device is disclosed in this application. In the following sections, detailed descriptions of various embodiments are described. The descriptions of various embodiments are illustrative embodiments, and various modifications and alterations may be apparent to those skilled in the art. Therefore, the exemplary embodiments do not limit the scope of this application. The digital element is designed for use in or adjacent to the body of a living organism.

Glossary

In the description and claims below, various terms may be used for which the following definitions will apply:

"Biocompatible" as used herein refers to a material or device that performs with an appropriate host response in a specific application. For example, a biocompatible device does not have toxic or injurious effects on biological systems.

"Communication System" as used herein, may refer to a wireless communication device that can be configured to transmit and receive information from a processor to a receiver in a smart hand held electronic device.

"Digital Element" as used herein, may refer to electronic components on a substrate.

"Smart Hand-held Device" as used herein, may refer to a smartphone or tablet built on a mobile operating system and having advanced processing capabilities.

"External Personal Hygiene Product" as used herein refers to but is not limited to Hygiene Products worn outside the body.

"Feminine Hygiene Product" as used herein refers to but is not limited to a tampon, sanitary pad, panty liner, nursing pad, or other product used to absorb or contain menstruation or bodily fluid discharge.

"Hygiene Product" as used herein refers to any absorbent material or device used by humans to absorb or contain bodily fluid discharge, including but not limited to Feminine Hygiene Products, diapers, men's guards and shields, adult diapers and booster pads.

"Power Source" as used herein refers to any device or layer which can supply energy or placing a logical or electrical device in an energized state. The power source may include batteries. The batteries can be formed from alkaline cell chemistry and may be solid-state batteries or wet cell batteries.

"Sensor Array" as used herein means a sensor or a plurality of sensors, which may include, for example, resistive or capacitive to detect liquid or moisture.

"Switch" as used herein means a circuit element that controls the flow of electrical current in response to a physical or electrical input Personal Hygiene Product with a Digital Element The present invention is an improvement of a Personal Hygiene Product with a digital element as disclosed in US2016/0250081 and U.S. Ser. No. 62/569,744, the entire contents of which are herein incorporated by reference.

External Personal Hygiene Product

Figure 1:
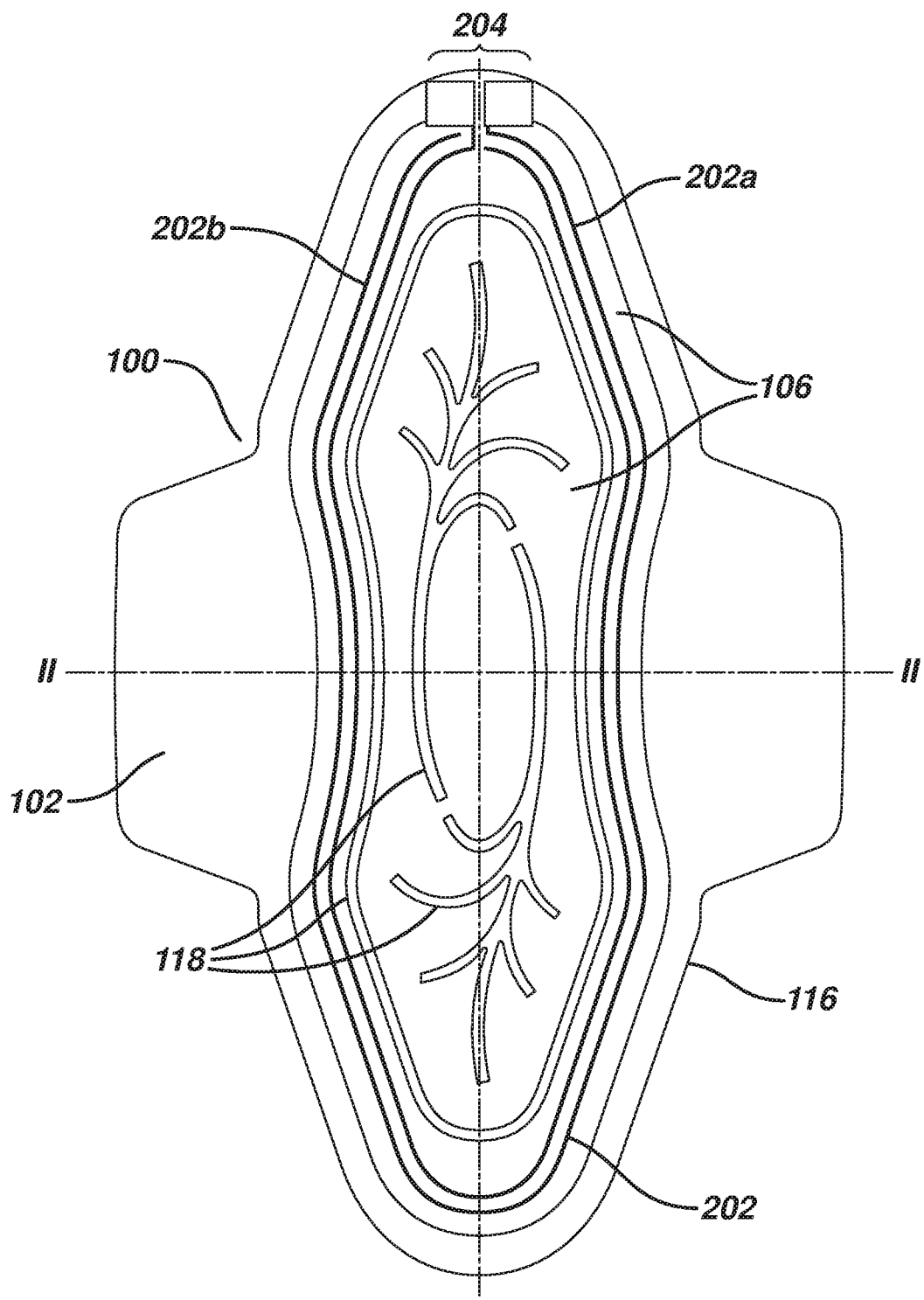
FIG. 1 illustrates a top plan view of an embodiment of personal hygiene product for use with a sensor element embedded in accordance with the present invention.
Figure 2:
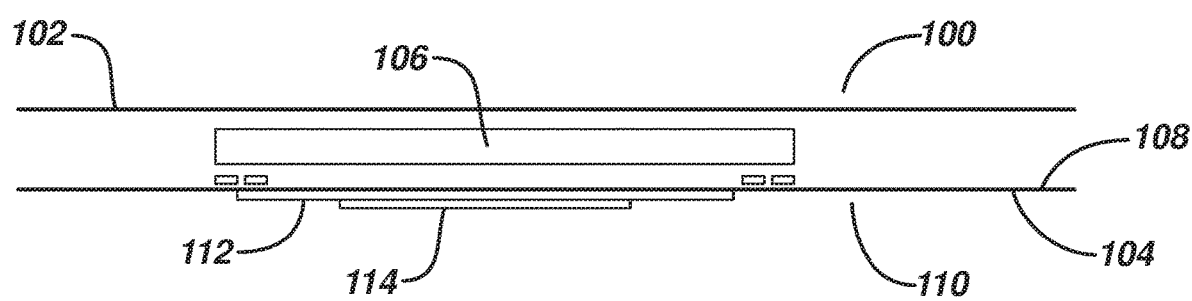
FIG. 2 illustrates an exploded cross-section along line II-II of the embodiment of FIG. 1.

Referring now to FIGS. 1-3, there is illustrated a Personal Hygiene Product 100 having a cover layer 102, a barrier layer 104, and an absorbent material 106 disposed between the cover layer 102, a barrier layer 104. The barrier layer 104 has an inner surface 108 directed toward the absorbent material 106 and an outer, garment-facing surface 110. The Personal Hygiene Product 100 may also have a positioning adhesive 112 disposed upon the outer surface 110 of the barrier layer 104. The positioning adhesive 112 may be protected by a release liner 114.

Figure 3A:
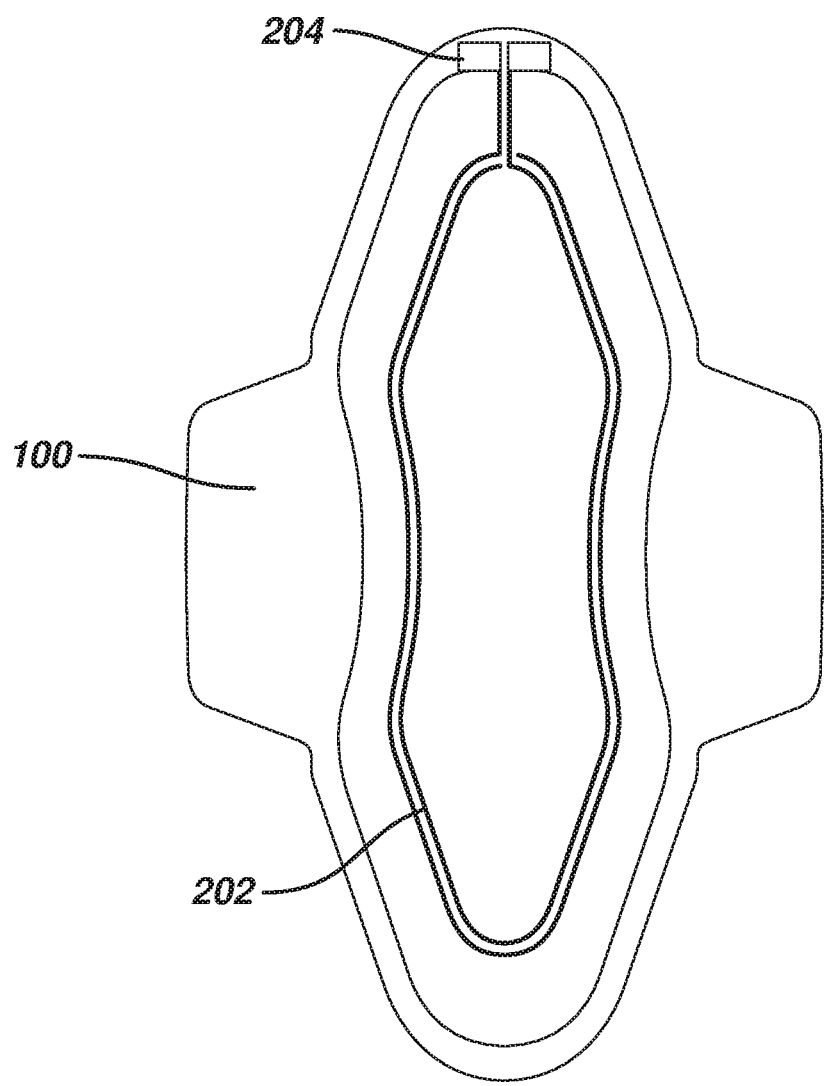
FIG. 3A is a diagrammatic representation of an exemplary feminine napkin with sensor.
Figure 3B:
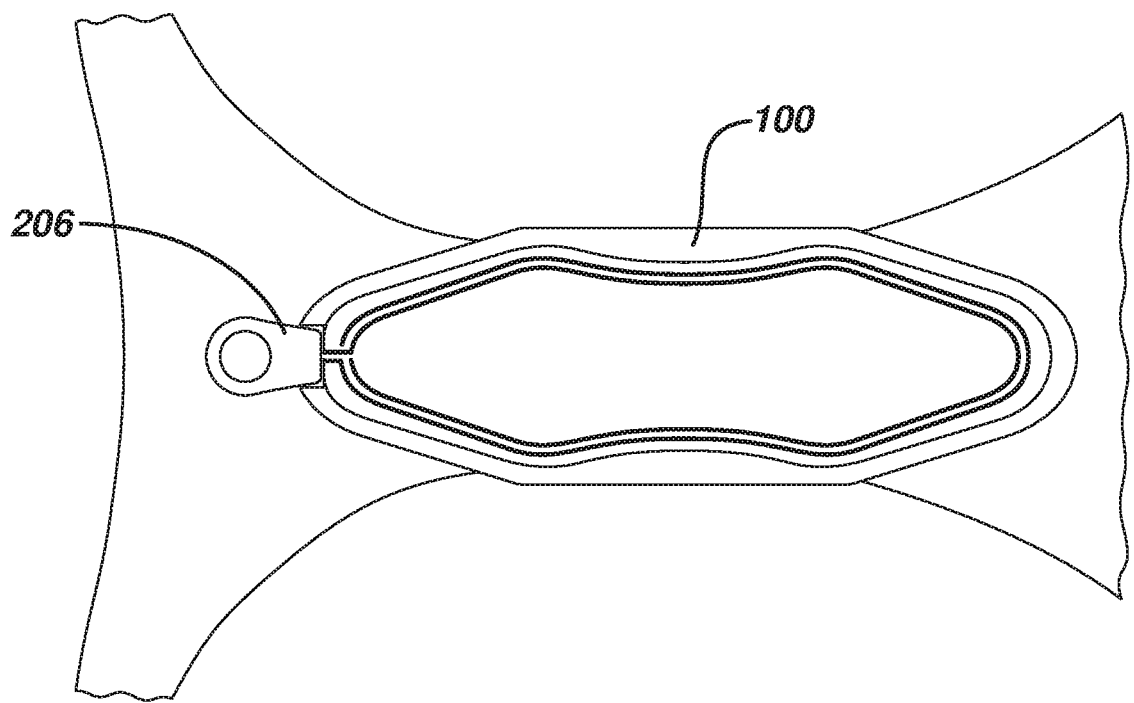
FIG. 3B is a diagrammatic representation of an exemplary attachment of a signal acquisition device to a feminine napkin and placement in underwear.
Figure 3C:
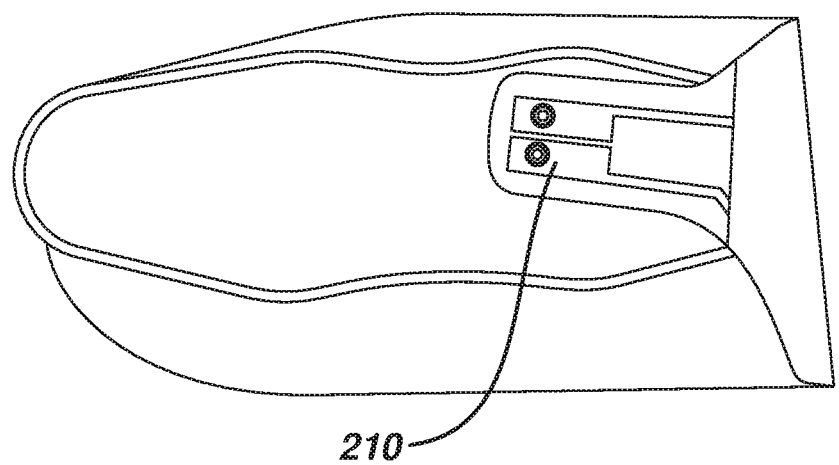
FIG. 3C shows an exemplary connector utilizing button snaps.

Referring now to FIG. 3, an external electronic feminine hygiene system for external sanitary products, such as sanitary napkins, liners, and incontinence pads is shown. FIG. 3A shows a Personal Hygiene Product 100 with embedded conductive elements, also referred to as sensor electrodes or traces 202. Such electrodes may be fabricated with conductive ink, metallized and transferred onto the pad, or through other methods. The ends of the traces 202 form a connection point or node 204. FIG. 3B shows said Personal Hygiene Product 100 with a signal acquisition device 206 attached, both against an undergarment. FIG. 3C shows an exemplary connector 208 in which metal button snaps 210 are crimped onto conductive traces 202 on the Personal Hygiene Product 100.

When fluid reaches the area between the two parallel traces 202, the resistance change is read by the tag and an alarm is triggered (e.g. vibration or message sent to a smartphone app). The transmission can be direct (using bluetooth, for example) or indirect (using a passive RFID). The transmission can be non-stop or a passive tag can be scanned directly by the smartphone, whenever the user desires. By continuous is meant a sampling rate of about 1 Hz.

Figure 4:
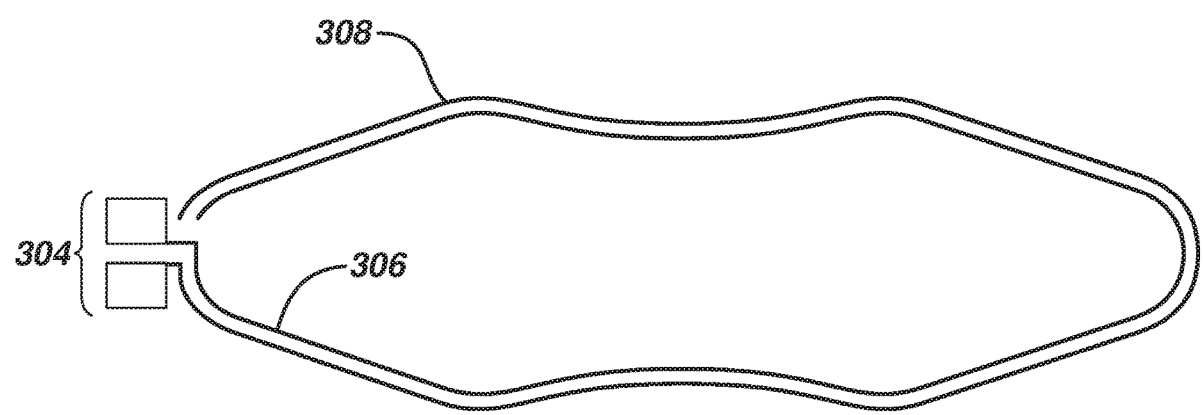
FIG. 4 is a top plan view of a personal hygiene product having a parallel sensor arrangement.

The traces 202 are in parallel arrangement, but are oriented in a mirrored configuration. Thus, trace 202a extends from the connection point 204 in a clockwise direction about the product, and trace 202b extends from the connection point 204 in a counter-clockwise direction about the product. This provides a constant signal due to a change in system resistance, no matter where the bridging between the traces 202 occurs. In contrast to a parallel arrangement shown in FIG. 4 in which a short-circuit proximate the node 304, e.g., at a point indicated at 306 would have a significantly different signal than a short-circuit distal the node 304, e.g., at a point indicated at 308.

The traces 202 may be disposed on any layer of the Personal Hygiene Product 100. In one embodiment, the traces 202 are disposed on the inner surface 108 of the barrier layer 104. Alternatively, the traces 202 may be disposed on or in the absorbent material 106 or the cover layer 102. However, we have found that conductive traces printed on porous fibrous substrates have a higher resistance due to ink adhesion and minimal gaps inherent in a porous fibrous structure. Preferably, the traces 202 are disposed on the inner surface 108 of the barrier layer 104. This separates the traces from contact with the user's body.

The traces 202 may be in the form of conductive ink (e.g. silver or carbon-based ink) printed or otherwise disposed on a substrate, a wire (e.g., copper, silver, carbon or other conductive material) disposed on or contained within one or more structures of the Personal Hygiene Product 100.

One or more regions of the Personal Hygiene Product 100 may be embossed as is known to those of ordinary skill in the art.

In one embodiment, the sensor traces 202 are disposed towards the outer margins 116 of the Personal Hygiene Product 100 and all embossments, e.g., 118, are disposed within a region defined by the sensor traces 202.

Figure 5:
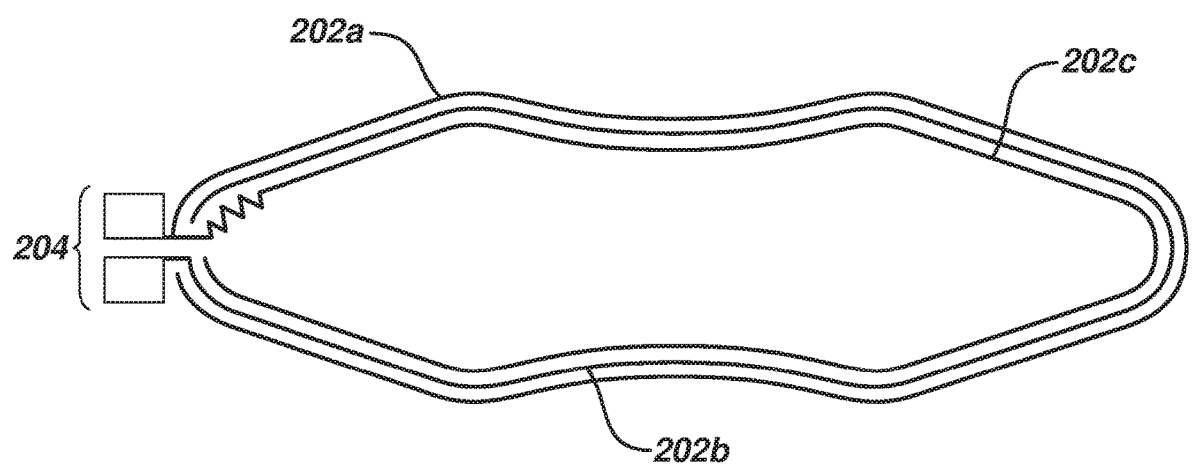
FIG. 5 is a diagrammatic representation of an alternative arrangement of the sensor element having three conductive traces.

In another embodiment shown in FIG. 5, a third conductive element 202c is disposed within the region defined by the sensor traces 202a, 202b. This provides an earlier warning of potential leakage than a simple pair of traces 202a, 202b.

Figure 6:
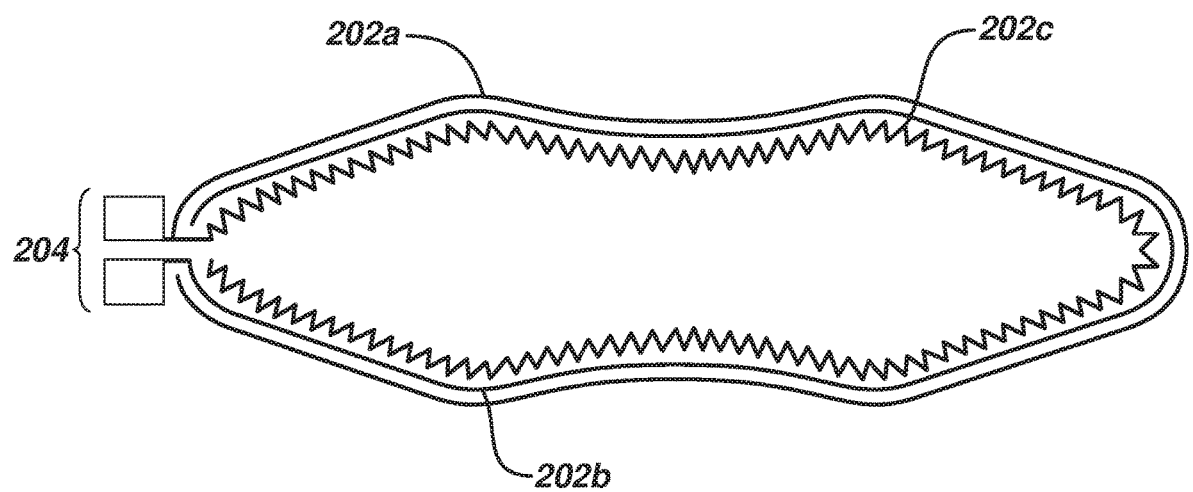
FIG. 6 is a diagrammatic representation of an alternative arrangement of the sensor element having three modified conductive traces.

The traces may be a continuous smooth line about the Personal Hygiene Product 100, or they may be as shown in FIG. 6. Although these angled line segment traces are shown for an embodiment including three conductive traces, similar angled line segment traces can be used for a pair of parallel traces.

Other Embodiments

The absorbent article may have an absorbent core, an embossing pattern and a humidity detection sensor and a resistance reader coupled to a wireless transmission element.

The Personal Hygiene Product may be used by connecting a resistance reader and wireless transmission device to each of the node or contacting zones of the sensor traces, synchronizing the wireless transmission device to an alarm device, reading the electrical resistance between the least two electrically conductive traces, and alerting when the resistance changes (from infinite to less than 1 Mega ohms).

Humidity detection sensor is located at the external periphery of the absorbent core, outside a zone defined by the embossing pattern and inside a zone defined by the edges of the absorbent core.

Connection of the humidity detection sensor to a resistance reader+ wireless transmission device Transmission of information to an alarm device, that will alert the user, preferred: Smartphone, smart watch or any mobile telecommunication device Width of the conductive ink traces from 0.1 mm to 5 mm (preferred between about 0.5 and about 1.5 mm, more preferred about 1 mm)

Spacing between adjacent conductive ink traces ranges from 0.1 mm to 5 mm (preferred between about 1.5 and about 2.5 mm, more preferred about 2 mm).

The electrically conductive traces are not in contact; the loop is open in its initial state and is closed when a liquid gets in contact with at least 2 tracks.

The connection node of the electrically conductive tracks have a surface of between about 65 mm$^2$ and about 225 mm$^2$, more preferably about 100 mm$^2$ (preferably between about 8 mm×8 mm and 15 mm×15 mm, most preferably about 10 mm×10 mm), located on the cover, or core, or backing layer, or on the upper side of the absorbent article.

Wireless transmission device may be built inside the pad or physically/electronically connected to it through the contacting zones Minimal distance between the electrically conductive tracks and the embossing pattern ranges between 0.1 mm to 5 mm (preferred 1 mm).

Resistance of the electrically conductive traces is less than 2000 ohms/sq, preferably about 100 ohms/sq.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but it should be constructed to cohere with all modifications that may fall within the scope of the appended claims.

What is claimed is:

1. A personal hygiene product with a digital element comprising:
   a) an external personal hygiene product to absorb bodily fluids having a perimeter; and
   b) a conductive sensor assembly disposed within the personal hygiene product, including a pair of conductive elements disposed in parallel in a mirrored image about the perimeter of the personal hygiene product wherein one of the pair of conductive elements extends from a connection point in a clockwise direction and terminates adjacent the connection point while the other one of the pair of conductive elements extends from the connection point in a counter-clockwise direction and terminates adjacent the connection point, and at least one connector directly contacting the pair of conductive elements, said conductive sensor assembly generating a signal indicative of fluid leakage of said personal hygiene product when fluid reaches the area between the pair of conductive elements;
wherein said conductive sensor assembly is arranged and configured to communicate with a smart hand held electronic device and wherein said pair of conductive elements are disposed in a single layer on the inner surface of the barrier layer.

2. The personal hygiene product of claim 1 wherein the personal hygiene product comprises a cover layer, a barrier layer, and an absorbent material disposed between the cover layer and barrier layer and wherein the barrier layer has an inner surface directed toward the absorbent material and an outer, garment-facing surface.

3. The personal hygiene product of claim 2 wherein each end of the conductive elements forms a connection node arranged and configured for connection to the conductive sensor assembly.

4. The personal hygiene product of claim 3 wherein the connection node of each conductive element has a surface area of between about 65 mm$^2$ and about 225 mm$^2$.

5. The personal hygiene product of claim 2 wherein the conductive elements comprise conductive ink.

6. The personal hygiene product of claim 2 wherein the conductive elements comprise wire.

7. The personal hygiene product of claim 2 further comprising one or more areas of embossments disposed within a region defined by the conductive elements.

8. The personal hygiene product of claim 1 further comprising a third conductive element disposed within the region defined by the pair of conductive elements.

9. The personal hygiene product of claim 1 wherein the conductive elements comprise connected, angled line segments.

10. The personal hygiene product of claim 1 wherein the conductive elements have a width of between about 0.1 mm and about 5 mm.

11. The personal hygiene product of claim 1 wherein the conductive elements are spatially separated by between about 0.1 mm and about 5 mm.

12. The personal hygiene product of claim 11 wherein the conductive elements are spatially separated by between about 1.5 mm and about 2.5 mm.

* * * * *